(12) United States Patent
Yue et al.

(10) Patent No.: US 8,952,040 B2
(45) Date of Patent: Feb. 10, 2015

(54) PHARMACEUTICAL COMPOSITION FOR TREATING COAGULATION DISORDER HEMORRHAGE AND METHOD USING THE SAME

(76) Inventors: Maoxing Yue, Bejing (CN); Honggui Wan, Jiangsu (CN); Tongge Huang, Jiangsu (CN)

(*) Notice: Subject to any disclaimer, the term of this patent is extended or adjusted under 35 U.S.C. 154(b) by 12 days.

(21) Appl. No.: 13/520,004

(22) PCT Filed: Dec. 10, 2010

(86) PCT No.: PCT/CN2010/079678
§ 371 (c)(1),
(2), (4) Date: Jun. 29, 2012

(87) PCT Pub. No.: WO2012/016408
PCT Pub. Date: Feb. 9, 2012

(65) Prior Publication Data
US 2013/0143836 A1    Jun. 6, 2013

(30) Foreign Application Priority Data

Aug. 6, 2010 (CN) .......................... 2010 1 0248451

(51) Int. Cl.
| | |
|---|---|
| A61K 31/198 | (2006.01) |
| A61K 31/714 | (2006.01) |
| A61K 31/51 | (2006.01) |
| A61K 31/4415 | (2006.01) |
| A61K 31/197 | (2006.01) |
| A61K 31/375 | (2006.01) |
| A61K 31/401 | (2006.01) |
| A61K 31/405 | (2006.01) |
| A61K 31/4172 | (2006.01) |
| A61K 31/4188 | (2006.01) |
| A61K 31/519 | (2006.01) |
| A61K 31/525 | (2006.01) |
| A61K 31/7004 | (2006.01) |
| A61K 31/52 | (2006.01) |

(52) U.S. Cl.
CPC ............. *A61K 31/714* (2013.01); *A61K 31/197* (2013.01); *A61K 31/198* (2013.01); *A61K 31/375* (2013.01); *A61K 31/401* (2013.01); *A61K 31/405* (2013.01); *A61K 31/4172* (2013.01); *A61K 31/4188* (2013.01); *A61K 31/4415* (2013.01); *A61K 431/455* (2013.01); *A61K 31/51* (2013.01); *A61K 31/519* (2013.01); *A61K 31/525* (2013.01); *A61K 31/7004* (2013.01); *A61K 31/52* (2013.01)
USPC ............................................ 514/354; 514/52

(58) Field of Classification Search
None
See application file for complete search history.

(56) References Cited

FOREIGN PATENT DOCUMENTS

| | | |
|---|---|---|
| CN | 1640396 A | 7/2005 |
| WO | WO 2007057748 A2 * | 5/2007 |

\* cited by examiner

*Primary Examiner* — Layla Bland
(74) *Attorney, Agent, or Firm* — Tim Tingkang Xia, Esq.; Morris, Manning & Martin, LLP

(57) ABSTRACT

Pharmaceutical composition for treating coagulation disorder hemorrhage. The pharmaceutical composition comprises (per unit): L-ornithine 0.5~8 g, aspartic acid 1~5 g, arginine 3~10 g and vitamin B6 3~10 g. A method of administrating the pharmaceutical composition to treat hemorrhage patients caused by coagulation dysfunction, especially critically ill patients.

6 Claims, No Drawings

PHARMACEUTICAL COMPOSITION FOR TREATING COAGULATION DISORDER HEMORRHAGE AND METHOD USING THE SAME

FIELD OF THE INVENTION

The present invention relates to the field of emergency treatment of critically ill patients, and more particularly to a pharmaceutical composition for treating coagulation disorder hemorrhage, and a method thereof to treat bleeding patients caused by coagulation disorder.

BACKGROUND OF THE INVENTION

In the case of severe trauma and infection, the blood system is often affected. The coagulation system abnormalities and dysfunction are very common in the clinical manifestations of systemic inflammatory response syndrome (SIRS) and multiple organ dysfunction syndrome (MODS). The blood system involvement in MODS ranks the top four in the organs involved in the literature reports and ranks the second in individual literature reports. The blood system abnormalities become the main cause and direct cause of the patents' death. The abnormal changes in the blood system during multiple organ dysfunction and failure are mainly divided into the changes in formed elements and the changes in coagulation and hemostatic functions. The coagulation dysfunction can be the inevitable result of disease occurrence and development and can also be induced by inappropriate treatment. In the case of massive hemorrhage caused by coagulation dysfunction in MODS, doctors are often helpless and most patients will die soon. Therefore, it is very important to research the key technologies for rescuing such dying patients.

Under normal circumstances, the coagulation process of organism is usually divided into intrinsic pathway, extrinsic pathway and common pathway.

The intrinsic coagulation pathway means that all the participatory coagulation factors come from the blood (intrinsic). When the vascular wall is injured, the subendothelial tissue is exposed and the negatively charged subendothelial collagenous fibers are in contact with the coagulation factors and combine with factor XII. factor XII is activated to become factor XIIa under the participation of HK and PK. Factor XIIa will activate factor XI without $Ca^{2+}$ and the activated factor XIa will activate factor IX with the presence of $Ca^{2+}$. Factor IXa itself activates factor X with fairly low effectiveness. As such, factor IXa shall be combined with factor VIIIa to form a 1:1 complex, also known as the factor X enzyme complex. $Ca^{2+}$ and PL are required in this reaction jointly. The intrinsic coagulation pathway, in fact, refers to the process from the activation of factor XII to the activation of factor X.

The extrinsic coagulation pathway means that not all the participatory coagulation factors exist in the blood and there are extrinsic coagulation factors participating in hemostasis. This process is initiated by exposing of tissue factor to the blood, till the activation of factor X. As a specific transmembrane protein existing in a variety of plasma membranes, tissue factors is released after the tissue is damaged and forms a 1:1 complex with factor VII with the participation of $Ca^{2+}$. Factor VII combined with the tissue factor will be soon activated by activated factor X to form VIIa. The extrinsic coagulation pathway is mainly adjusted by tissue factor pathway inhibitor (TFPI). TFPI is a kind of glycoprotein existing in normal human plasma, blood platelets and vascular endothelial cell. TFPI forms complex with factor Xa or factor VIIa-tissue factor-factor Xa to inhibit the activity of factor Xa or factor VIIa-tissue factor. In addition, studies have shown that intrinsic coagulation and extrinsic coagulation pathways can be activated mutually.

From the activation of factor X to the formation of fibrin is the common coagulation pathway of intrinsic and extrinsic coagulation, mainly including two stages including thrombin generation and fibrin formation.

(1) Thrombin generation: factor Xa and factor Va form prothrombin complex, i.e., thrombokinase in the presence of $Ca^{2+}$ and phospholipid membranes. Thrombokinase transforms prothrombin into thrombin.

(2) Fibrin formation: fibrinogen is decomposed into fibrin monomers by the enzymolysis of thrombin and forms stable fibrin clot by cross-linking. This process can be divided into three stages, fibrin monomer generation, fibrin monomer polymerization and fibrin cross-linking. Hydrolyzing by thrombin, the negatively charged fibrinopeptide A and fibrinopeptide B are removed from fibrinogen to form fibrin monomers. After generation, the fibrin monomers are combined by non-covalent bonds to form fibrin polymer, also known as soluble fibrin. After generation, the fibrin can promote the activation of factor XIII by thrombin. With the involvement of XIIIa and $Ca^{2+}$, the adjacent fibrins are cross-linked rapidly to form the insoluble stable fibrin clots.

Since pathogenesis of MODS has not been fully elucidated and no breakthrough has been made in regards to the clinical treatment of MODS, the fatality rate of MODS patients remains high, especially for patients with coma, emergency ulcer massive hemorrhage, etc. resulted from MODS, where traditional coagulation drugs can not play the role directly, and extracorporeal circulation adjuvant therapy at high cost are generally used to support the organs.

It is reported that four major coagulation factors (factor II, factor V, factor VII and factor VIII) in the coagulation system are synthesized by liver. Under MODS, the hyperbilirubinemia exists, aminotransferases (ALT or AST) rise, LDH rises, hypobilirubinemia exists, prothrombin time is prolonged, jaundice and flapping tremor exists; platelet count is less than 80000/μl or falls by over 50% in three days; arterial blood pressure ≤90 mmHg or the mean arterial blood pressure is ≤70 mmHg, accompanied with tachycardia, arrhythmia, cardiac arrest and so on. The existence of a variety of harmful free radicals aggravates the damages to the organs and especially brings series damage to liver, resulting in increased blood ammonia concentration, slow metabolism, blocked synthesis of key enzymes and important factors (4 major coagulation factors) and bringing life threat to the patients in massive hemorrhage under MODS.

CONTENT OF THE INVENTION

One purpose of the present invention is to provide a pharmaceutical composition used to treat hemorrhage caused by coagulation disorder.

Another purpose of the present invention is to provide a use of the above pharmaceutical composition.

Another purpose of the present invention is to provide a method to treat the hemorrhage patients due to coagulation disorder by means of the above pharmaceutical composition.

The action mechanism of the present invention are as follows. Large dose of vitamin B6 is a protective agent for brain and nerve and vitamin B6 is also a natural diuretic. It is know that vitamin B6 is required for more than 60 enzymes. With vitamin C, vitamin B6 can remove the harmful free radicals generated by MODS and quickly reduce the poison of free oxygen to the organs. The compound amino acids containing L-ornithine, aspartic acid and arginine can provide appropriate substrates for intrinsic coagulation mechanism. With the included high branched chain amino acid, it can not only correct the metabolic imbalance between the branched chain amino acids and aromatic amino acids, but also inhibit the formation of false neurotransmitters in the brain and improve hepatic encephalopathy. L-ornithine itself can quickly penetrate the mitochondrial membrane, carry a molecule of carbon dioxide and a molecule of ammonia to transform into L-citrulline through metabolism in the mitochondria, rapidly activate the urea cycle in liver cells with L-aspartic acid after rapidly passing through the mitochondria and discharge the harmful carbon dioxide and ammonia generated under MODS outside the body by ornithine metabolism (urea cycle), resulting in the gradual recovery of enzyme metabolism in the liver, the generation of the four major coagulation factors and rapid recovery of intrinsic coagulation pathway. Cooperating with conventional treatment, this method can effectively treat the dying patients in massive hemorrhage due to coagulation disorders.

The purposes of the present invention are achieved through the following technical schemes.

A pharmaceutical composition used to treat coagulation disorder hemorrhage, contains L-ornithine 0.5~8 g, aspartic acid 1~5 g, arginine 3~10 g and vitamin B6 3-10 g per unit.

The pharmaceutical composition, further contains one or more of the following substances per unit: isoleucine, leucine, lysine, methionine, phenylalanine, threonine, tryptophan, valine, histidine, glycine, alanine, proline, asparagine, cysteine, glutamic acid, serine, tyrosine, VitB1, VitB2, VitB3, pantothenic acid, biotin, folic acid, VitB12 and vitamin C.

Among them, the dosages of amino acids are respectively: isoleucine 3~10 g, leucine 5~15 g, lysine 3~10 g, methionine 0.5~3 g, phenylalanine 0.5~3 g, threonine 3~10 g, tryptophan 0.5~3 g, valine 5~15 g, histidine 3~8 g, glycine 3~8 g, alanine 3~10 g, proline 3~8 g, asparagine 0.1~3 g, cysteine 0.1~3 g, glutamic acid 3~10 g, serine 0.5~5 g, tyrosine 0.1~3 g. The dosages of B vitamins are respectively: VitB1 1~2 mg, VitB2 1~2 mg, VitB3 10~20 mg, pantothenic acid 3~5 mg, biotin 0.1~0.2 mg, folic acid 0.1~0.4 mg, VitB12 2~6 µg; vitamin C 1-3 g.

The pharmaceutical composition, also contains an appropriate amount of 5% glucose and sodium chloride injection or 0.9% sodium chloride injection.

The application of the pharmaceutical composition in the preparation of drugs used to treat coagulation disorder hemorrhage.

A method to treat hemorrhagic patients caused by coagulation disorders, in which the above pharmaceutical composition is infused at appropriate time.

The treatment method are as follows. For patients with mild hemorrhage, 0.5~1 unit of the above pharmaceutical composition is administered by 30 minutes to 6 hour intravenous infusion each day, and dosed for 1-9 consecutive days. For patients with severe hemorrhage, 0.5~1 unit of the above pharmaceutical composition is administered by a 20-30 minute intravenous infusion each day, and dosed for 1-5 consecutive days, and after symptom improvement, followed by the treatment for patients with mild hemorrhage. For patients with extra severe hemorrhage, 1~2 units of the above pharmaceutical composition is administered by a 10-15 minute rapid intravenous infusion to central vein ach day, and dosed for 1-5 consecutive days, and after symptom improvement, followed by the treatment for patients with mild hemorrhage.

The amino acids in the present invention are L-amino acids unless expressly stated.

BENEFICIAL EFFECTS OF THE PRESENT INVENTION

The present invention ingeniously uses shock therapy with compound amino acid injection containing L-ornithine, aspartic acid and arginine+a large dose of B vitamins, and combined with vitamin C according to the patients' conditions, efficiently opens up the body's metabolic pathways under MODS state and provides a cost-effective method for saving the dying patients in coagulation disorder hemorrhage. This method has not been reported in the literature at home and abroad.

By using the shock therapy with the compound amino acid injection containing L-ornithine, aspartic acid and arginine+a large dose of B vitamins to treat hundreds of emergency and critical disease patients, the total protein (TP), albumin (ALB), total bilirubin (TBIL), indirect bilirubin (IBIL), alanine transaminase (ALT) and aspartate aminotransferase (AST) have declined significantly, the improvement of coagulation function, rise of HB and improvement of immunologic function is significant, and globulin (GLB), white/ball (A/B) and direct bilirubin (DBIL) have no significant change. It can be seen that the new therapy with the compound amino acid injection containing L-ornithine, aspartic acid and arginine combined with a large dose of B vitamins can really play an important role in the treatment of critical diseases and is quite helpful to the recovery of liver function, improvement of coagulation function, rise of HB and improvement of immunological function.

On the basis of conventional treatment, the shock therapy of the compound amino acid injection containing L-ornithine, aspartic acid and arginine combined with a large dose of B vitamins can be creatively used for treatment of the following patients.

1) Hemorrhagic patients with coagulation dysfunction due to infectious and non-infectious factors (severe trauma, severe acute pancreatitis, major surgery, cardiopulmonary resuscitation, pathological pregnancy, etc.), which may cause MODS.

2) Hemorrhagic patients caused by concurrent coagulation dysfunction with abnormal liver function.

3) Hemorrhagic patients caused by concurrent coagulation dysfunction with other diseases. It also has secondary efficacy for the organism's metabolic disturbance caused by severe trauma, especially the multiple organ failure under MODS state.

EMBODIMENT OF THE INVENTION

The present invention is further elaborated through the following embodiments.

Embodiment 1

Statistics of Clinical Treatment

I. Case inclusion criteria.

(1) Hemorrhagic patients with the pathogens causing MODS and caused by coagulation dysfunction due to infectious and non-infectious factors (severe trauma, severe acute pancreatitis, major surgery, cardiopulmonary resuscitation, pathological pregnancy, etc.).

(2) The system and organ disorder occurs when the integral of single organ damage is no less than 1 and the system and organ failure occurs when the integral of single organ damage is no less than 3 according to Marshall Standard (Table 1) 24 hours after the occurrence of above factors.

(3) Age between 18 and 86.

(4) Hemorrhagic patients caused by the coagulation dysfunction due to MODS and liver dysfunction.

In the present invention, the judgment standard for the mild patients, severe patients and extra severe patients is the marking criteria development by Canadian professor Marshall in 1995. The higher the score, the more serious the illness condition, as shown in Tables 1 and 2.

TABLE 1

MODS Marking Criteria (Marshall, 1995)

|  | 0 | 1 | 2 | 3 | 4 |
|---|---|---|---|---|---|
| Respiratory system ($PaO_2/FIO_2$) | >300 | 226-300 | 151-225 | 76-150 | ≤75 |
| Kidney (Serum creatinine μmol/L) | ≤100 | 101-200 | 201-350 | 351-500 | >500 |
| Liver (Hemobilirubin mg/L) | ≤20 | 21-60 | 61-120 | 121-240 | >240 |
| Cardiovascular (PAR) | ≤10.0 | 10.5-15.0 | 15.1-20.0 | 20.1-30.0 | ≥30.0 |
| Blood (Blood platelet × $10^9$) | >120 | 80-120 | 51-80 | 21-50 | ≤20 |
| Central nervous system (Glasgow Marking) | 15 | 13-14 | 10-12 | 7-9 | ≤6 |

Note:
PAR (heart rate after pressure adjustment) = heart rate × right atrial (central vein) pressure/ mean blood pressure

TABLE 2

Judgment of Hemorrhagic Shock Degree and Estimated Blood Loss

| Shock degree* | Mild (compensatory stage) | Severe patients | Extra severe patients |
|---|---|---|---|
| Consciousness | Lucid | Faint | Blurred |
| Skin color, temperature |  | Pale, cold | Gray, wet cold |
| Superficial vein |  | Shrinkage, thinning | Collapse |
| Pulse (beats/min) | Faster | 100~120 | >120, thin and delicate |
| Systolic blood pressure | Normal | 70~90, narrow pulse pressure | <70, narrower pulse pressure |
| Urine volume |  | Oliguria | <25 ml/h |
| Estimated blood loss (ml)** | 600~800 | 800~1600 | >1600 |
| Ratio of hemorrhage volume to total blood volume (%) | 20 | 35 | >40 |

*The mild shock is in the shock compensatory stage and the medium and severe shock is in the shock decompensatory stage.
**Calculated by the blood volume of 7% of the weight, such as a wounded person of 50 kg with the blood volume of 4000 ml, the hemorrhage volume of 700 ml is 20% of the weight.

Combined with Tables 1 and 2, the mild patients are with the MODS marking of level 0~1, the severe patients are with the MODS marking of level 2~3 and the extra severe patients are with the MODS marking of level 4. The illness conditions of the patients are distinguishes as mild, severe and extra severe according to the representation of hemorrhagic shock.

II. Exclusion criteria.

(1) Patients died or discharged with the treatment of no more than 24 hours; and (2) patients fails to adhere to systemic treatment.

III. Judgment criteria for coagulation function improvement.

(1) Extract 15 ml venous blood after treatment for 0, 1, 4, 7, 14 and 28 days, centrifuge at the speed of 3000 rev/min, separate serum and store in a low-temperature refrigerator for uniform testing.

(2) Detect PLT, D-Dimer, FDP, Fib, whole blood coagulation time (CT).

(3) Observe the time when actual hemorrhage stops.

(4) Liver: ALT, AST, PT and prothrombin activity, TBIL, albumin and cholinesterase.

IV. Judgment criteria for curative effect.

1. Ineffective: there is no effect or the coagulation function is only slightly improved and the hemorrhage symptom can not be relieved in combination with conventional treatment.

2. Effective: the coagulation function of the mild patients is significantly improved in combination with conventional treatment and the hemorrhage symptom is relieved within 1-9 days. 3. Tangibly effective: the coagulation function of the severe and extra severe patients significantly improved in combination with conventional treatment and the hemorrhage symptom stops within 1-5 days.

The conventional treatment in the present invention refers to the use of haemostatic drugs for hemorrhagic patients, including platelets, prothrombin complexes, cryoprecipitation, plasma and a series of haemostatic methods. The aorta rupture hemorrhage has been stanched through surgeries.

V. Treatment methods.

Per unit pharmaceutical composition contains: L-ornithine 0.5~8 g, aspartic acid 1~5 g, arginine 3~10 g and vitamin B6 3-10 g.

Per unit pharmaceutical composition also contains one or more of the following substances: isoleucine 3~10 g, leucine 5~15 g, lysine 3~10 g, methionine 0.5~3 g, phenylalanine 0.5~3 g, threonine 3~10 g, tryptophan 0.5~3 g, valine 5~15 g, histidine 3~8 g, glycine 3~8 g, alanine 3~10 g, proline 3~8 g, asparagine 0.1~3 g, cysteine 0.1~3 g, glutamic acid 3~10 g, serine 0.5~5 g, tyrosine 0.1~3g; the dosages of B vitamins are respectively: VitB1 1~2 mg, VitB2 1~2 mg, VitB3 10~20 mg, pantothenic acid 3~5 mg, biotin 0.1~0.2 mg, folic acid 0.1~0.4 mg, VitB12 2~6 μg; vitamin C 1-3g.

The above substances can be added in 250 ml~500 ml of 5% glucose and sodium chloride injection or 0.9% sodium chloride injection (0.9% sodium chloride injection for diabetic patients).

Combined with conventional treatment, the mild patients use 1 unit of the above pharmaceutical composition each day and are dosed with intravenous infection for 1-9 consecutive days with 30 minutes to 6 hours each day.

Combined with conventional treatment, the severe patients use 0.5~1 unit of the above pharmaceutical composition each day, are dosed with intravenous infection for 1-5 consecutive days with 20-30 minutes each day and use the treatment method of mild patients as above after symptoms improve.

Combined with conventional treatment, the extra severe patients use 1~2 units of the above pharmaceutical composition each day, are rapidly dosed in central vein for 1-5 consecutive days with 10-15 minutes each day and use the treatment method of mild patients as above after symptoms improve.

VI. Treatment effect.

Select 156 cases of mild patients, 68 cases of severe patients and 21 cases of extra severe patients with 169 male and 76 female, the age of 18~86 and the average age of 57;

180 effective cases, 55 tangibly effective cases, 8 ineffective cases and 2 excluded cases.

Embodiment 2

Presentation of Specific Cases

1. Mr. Zhu, 66 years old, with gallstones, had normal coagulation function before surgery. He was satisfied with the treatment of blood vessels and gallbladder bed in the cholecystectomy which was operated smoothly. Everything was normal in the morning on the day of the surgery and he vomited in the evening and then the blood appeared in the abdominal drain tube with faster heartbeat and decreased blood pressure. He was operated on again in that evening. It was found in the surgery that the vascular ligature did not fall off and only there were hemorrhagic spots in the gallbladder bed with peripheral edema, which was suspected to be caused by tear after vomit. The gallbladder bed was carefully stitched and rinsed repeatedly. The abdomen was closed and the surgery was completed after all medical personnel beside the operating table observed for half and hour and confirmed no hemorrhage. At that night and the next morning, the abdominal drainage amount was not much and normal, but in the evening the abdominal drainage amount was significantly increased and the hemorrhage was obvious, so the third surgery was conducted. There were no obvious hemorrhagic spots in the abdominal cavity after it was opened, and only the liver, the liver surrounding tissues and the retroperitoneum had obvious edema with slow hematopedesis. The hemostasis by compression, stitch hemostasis, electric coagulation hemostasis and other conventional means did not work. Thus, the patient was continuously dosed with a large number of hemostatic drugs, including platelets, prothrombin complexes, cryoprecipitation, plasma, etc. Then the hemorrhage was decreased slightly but continued. He was treated and cured by means of shock therapy of compound amino acid injection 500 ml (including L-ornithine 2.80 g, aspartic acid 2.50 g, arginine 8.50 g, isoleucine 7.80 g, leucine 12.50 g, lysine 7.50 g, methionine 1.80 g, phenylalanine 1.60 g, threonine 4.60 g, histidine 4.50 g, glycine 5.50 g, proline 6.60 g, asparagine 1.20 g, cysteine 0.80 g, glutamic acid 5.90 g, tyrosine 1.20 g) and a large dose of vitamin B6 (250 mL 5% sodium chloride and dextrose injection added with 50 pieces of vitamin B6 (5 g) and 2 pieces of vitamin C (2 g) on the basis of conventional hemostatic measures and was given venous transfusion for 30 min. Half an hour later, the patent's liver and the surrounding edema had subsided and the abdominal hemorrhage had also been reduced. An hour later, the hemorrhage was less, so the abdomen was closed and the surgery was completed. The patient was successfully discharged after the surgery.

2. Mr. Fang, 41 years old, was subject to splenectomy and portal azygos disconnection surgeries four months ago due to cirrhosis, portal hypertension, hypersplenism, esophageal phleborrhexis massive hemorrhage. The massive hemorrhage appeared again after the surgery and the patient was discharged after active treatment in stable condition. The massive hemorrhage appeared again after a bath four days ago and the lowest hemachrome was 4.8 g. The massive hemorrhage appeared again after the illness state was stable one. After blood transfusion, plasma transfusion, protein and hemostatic drugs, the patient's hemachrome was increased to 7.3 g, but still with a large number of ascites, renal insufficiency and massive hemorrhage. The critical condition process of the patient was inhibited by means of immune nutritional support, microcirculation, and antagonism of inflammatory mediators, gradual recovery with metabolic enzymes and other treatment measures with the method of local and systemic treatment combination according to the illness condition. The patient used diuretic measures appropriately, used compound amino acid injection 500 ml each day (including L-ornithine 1.85 g, aspartic acid 2.50 g, arginine 8.80 g, isoleucine 8.80 g, leucine 13.60 g, lysine 7.51 g, phenylalanine 1.60 g, threonine 4.60 g, tryptophan 1.50 g, valine 10.60 g, histidine 4.70 g, glycine 6.30 g, alanine 8.30 g, proline 7.10 g, asparagine 0.48 g, glutamic acid 5.70 g, serine 3.70 g, tyrosine 0.67 g) and vitamin B6 8 g (added to 250 mL 5% sodium chloride and dextrose injection), and was given venous transfusion for 4 consecutive days with 2 hours each day by means of shock therapy. The patient's condition had been stabilized and then the hemorrhage stopped and the patient was saved.

3. Ms. Yang, 85 years old with the patient number of 752, had extensive cerebral infarction, severe diabetes and serious pulmonary infection causing MODS and coma for five days. The critical condition process of the patient was inhibited by means of immune nutritional support, microcirculation, and antagonism of inflammatory mediators, gradual recovery with metabolic enzymes and other treatment measures. The patient used the compound amino acid injection 500 mL each day (including L-ornithine 4.50 g, aspartic acid 2.80 g, arginine 8.50 g, isoleucine 7.50 g, leucine 10.80 g, lysine 8.50 g, methionine 1.60 g, phenylalanine 2.00 g, threonine 4.60 g, tryptophan 1.50 g, valine 10.50 g, histidine 4.70 g, glycine 6.30 g, alanine 8.00 g, proline 6.50 g, asparagine 0.60 g, cysteine 0.80 g, glutamic acid 5.00 g, serine 3.50 g, tyrosine 1.60 g)+vitamin B6 10 g+vitamin B1 1.5 mg+vitamin B2 1.5 mg+vitamin C 2 g (vitamin was added to 250 mL 0.9% sodium chloride injection), and was given venous transfusion for 2 consecutive days with 30 minutes each day by means of shock therapy in combination with a short-range large dose of anisodamine and dexamethasone (3 consecutive days with 0.66 mg/kg/time respectively and 3 times/day). The conjunctive use of a large dose of anti-aerobic and anti-anaerobic antibiotics made Ms. Yang, an extra severe patient through the strike of MODS and thus come around. The patient was improved by continuous use of the above compound amino acid injection 500 ml+vitamin B6 10 g+vitamin C 2 g for 3 consecutive days with 3 hours each day.

4. Mr. Lee, 84 years old, required long-term dialysis every two days due to chronic renal failure and had cerebral infarction, hypertension and severe diabetes. The patient was in a coma as the gastrointestinal tract appeared stress ulcer hemorrhage due to MODS caused by severe pulmonary infection. The key technology used to rescue the dying wounded was intended to use, that is, the patient used the compound amino acid injection 500 mL each day (including L-ornithine 3.5 g, aspartic acid 2.50 g, arginine 8.80 g, isoleucine 8.80 g, leucine 13.60 g, lysine 7.51 g, methionine 1.20 g, phenylalanine 1.60 g, threonine 4.60 g, tryptophan 1.50 g, valine 10.60 g, histidine 4.70 g, glycine 6.30 g, alanine 8.30 g, proline 7.10 g, asparagine 0.48 g, cysteine 0.59 g, glutamic acid 5.70 g, serine 3.70 g, tyrosine 0.67 g)+vitamin B 6 5 g+vitamin C 2 g (vitamin was added to 250 mL 0.9% sodium chloride injection) and was given venous transfusion for 3 consecutive days with 30 minutes each day by means of shock therapy with the method of local and systemic treatment combination. The successful method stopped the stress ulcer hemorrhage and the patient came around with stable vital signs. The patient was improved by continuous use of the above compound amino acid injection 500 ml+vitamin B6 6 g+vitamin C 2 g for 5 consecutive days with 4 hours each day.

Embodiment 3

Pharmaceutical Composition Preparation

A pharmaceutical composition with the components of compound amino acid injection containing 5 kinds of amino acids (in which, L-ornithine content of 1.5 g, L-aspartic acid content of 2.5 g, L-arginine content of 8.5 g, L-serine content of 3.8 g and L-threonine content of 4.6 g) and Vit B6 8 g.

Embodiment 4

Pharmaceutical Composition Preparation

A pharmaceutical composition with the components of compound amino acid injection 500 mL (including L-ornithine 3.5 g, aspartic acid 2.50 g, arginine 8.80 g, isoleucine 8.80 g, leucine 13.60 g, lysine 7.51 g, methionine 1.20 g, phenylalanine 1.60 g, threonine 4.60 g, tryptophan 1.50 g, valine 10.60 g, histidine 4.70 g, glycine 6.30 g, alanine 8.30 g, proline 7.10 g, asparagine 0.48 g, cysteine 0.59 g, glutamic acid 5.70 g, serine 3.70 g, tyrosine 0.67 g), Vit B6 3-10 g, Vit C 1-3 g and 0.9% sodium chloride injection 250 mL with vitamin added.

Embodiment 5

Pharmaceutical Composition Preparation

A pharmaceutical composition with the components of compound amino acid injection 500 mL (including L-ornithine 4.5 g, aspartic acid 2.80 g, arginine 8.30 g, isoleucine 6.50 g, leucine 12.00 g, lysine 7.50 g, methionine 1.60 g, phenylalanine 1.40 g, tryptophan 1.80 g, valine 10.60 g, histidine 4.80 g, glycine 6.20 g, alanine 8.50 g, proline 7.10 g, asparagine 0.48 g, glutamic acid 5.70 g, serine 3.70 g, tyrosine 0.67 g), Vit B6 3-10 g, VitB1 1~2 mg, VitB2 1~2 mg, VitB3 10~20 mg, pantothenic acid 3~5 mg, biotin 0.1~0.2 mg, folic acid 0.1~0.4 mg, VitB12 2~6 µg; Vit C 1-3 g and 5% sodium chloride and dextrose injection 250 mL with vitamin added.

Embodiment 6

Pharmaceutical Composition Preparation

A pharmaceutical composition with the components of compound amino acid injection 500 mL (including L-ornithine 2.5 g, aspartic acid 2.50 g, arginine 8.80 g, isoleucine 6.80 g, leucine 11.50 g, lysine 7.50 g, methionine 1.60 g, phenylalanine 1.30 g, threonine 4.40 g, tryptophan 1.70 g, histidine 4.60 g, glycine 6.30 g, alanine 8.30 g, proline 6.20 g, asparagine 0.60 g, cysteine 0.80 g, glutamic acid 5.70 g, serine 3.70 g, tyrosine 1.10 g), VitB1 1~2 mg, VitB2 1~2 mg, Vit B6 3-10 g, Vit C 1-3 g, and 5% sodium chloride and dextrose injection 250 mL with vitamin added.

What is claimed is:

1. A method for treating a hemorrhagic patient caused by coagulation disorders, comprising:
    infusing a pharmaceutical composition to the patient,
    wherein the pharmaceutical composition comprises L-ornithine 0.5~8 g, aspartic acid 1~5 g, arginine 3~10 g, and vitamin B6 3~10 g per unit; and
    wherein the pharmaceutical composition is capable of promoting coagulation of the patient.

2. The method according to claim 1, wherein when the patient has mild hemorrhage, the method comprises:
    administrating 0.5~1 unit of the pharmaceutical composition by a 30 minutes to 6 hour intravenous infusion each day for 1 to 9 consecutive days to the patient.

3. The method according to claim 1, wherein when the patient has severe hemorrhage, the method comprises sequentially:
    administrating 0.5~1 unit of the pharmaceutical composition by a 20 to 30 minutes intravenous infusion each day for 1 to 9 consecutive days to the patient; and
    administrating 0.5~1 unit of the pharmaceutical composition by a 30 minutes to 6 hour intravenous infusion each day for 1 to 9 consecutive days to the patient.

4. The method according to claim 1, wherein when the patient has extra severe hemorrhage, the method comprises sequentially:
    administrating 1~2 unit of the pharmaceutical composition by a 10 to 15 minutes intravenous infusion to central vein each day for 1 to 5 consecutive days to the patient; and
    administrating 0.5~1 unit of the pharmaceutical composition by a 30 minutes to 6 hour intravenous infusion each day for 1 to 9 consecutive days to the patient.

5. The method according to claim 1,
    wherein the pharmaceutical composition-further comprises one or more compounds selected from the group consisting of isoleucine, leucine, lysine, methionine, phenylalanine, threonine, tryptophan, valine, histidine, glycine, alanine, proline, asparagine, cysteine, glutamic acid, serine, tyrosine, VitB1, VitB2, VitB3, pantothenic acid, biotin, folic acid, VitB12, and vitamin C,
    wherein dosages of amino acids are respectively: isoleucine 3~10 g, leucine 5~15 g, lysine 3~10 g, methionine 0.5~3 g, phenylalanine 0.5~3 g, threonine 3~10 g, tryptophan 0.5~3 g, valine 5~15 g, histidine 3~8 g, glycine 3~8 g, alanine 3~10 g, proline 3~8 g, asparagine 0.1~3 g, cysteine 0.1~3 g, glutamic acid 3~10 g, serine 0.5~5 g, tyrosine 0.1~3 g, VitB1 1~2 mg, VitB2 1~2 mg, VitB3 10~20 mg, pantothenic acid 3~5 mg, biotin 0.1~0.2 mg, folic acid 0.1~0.4 mg, VitB12 2~6 µg, and vitamin C 1~3 g.

6. The method according to claim 1, wherein the pharmaceutical composition-further comprises an appropriate amount of 5% glucose and sodium chloride injection or 0.9% sodium chloride injection.

* * * * *